United States Patent [19]

Dory

[11] Patent Number: 4,991,151
[45] Date of Patent: Feb. 5, 1991

[54] ELASTIC PULSE GENERATOR HAVING A DESIRED PREDETERMINED WAVE FORM

[75] Inventor: Jacques Dory, Coupvray, France

[73] Assignee: EDAP International, France

[21] Appl. No.: 187,177

[22] Filed: Apr. 28, 1988

Related U.S. Application Data

[60] Continuation-in-part of Ser. No. 37,369, Apr. 13, 1987, abandoned, which is a division of Ser. No. 728,905, Apr. 30, 1985, Pat. No. 4,658,828, which is a continuation-in-part of Ser. No. 674,889, Nov. 26, 1984, Pat. No. 4,617,931.

[30] Foreign Application Priority Data

Apr. 28, 1987 [FR] France ............................ 87 05980

[51] Int. Cl.$^5$ .......................................... H04R 1/02
[52] U.S. Cl. .................................. 367/150; 367/155; 128/24 A; 73/625
[58] Field of Search ............... 367/103, 119, 123, 129, 367/150, 151, 155, 156, 157, 164, 165, 168; 128/328, 660, 663.01, 662.03, 24 A; 310/316; 73/625

[56] References Cited

U.S. PATENT DOCUMENTS

| | | | |
|---|---|---|---|
| 4,012,952 | 3/1977 | Dory | 73/67.7 |
| 4,217,516 | 8/1980 | Iinuma et al. | 310/335 |
| 4,271,490 | 6/1981 | Mihohara et al. | 367/122 |
| 4,478,085 | 10/1984 | Sasahi | 128/660 X |
| 4,526,168 | 7/1985 | Hassler et al. | 128/24 A X |
| 4,617,931 | 10/1986 | Dory | 128/304 |
| 4,618,796 | 10/1986 | Riedlinger | 310/311 |
| 4,626,728 | 12/1986 | Flachenecker et al. | 310/316 |
| 4,639,904 | 1/1987 | Riedlinger | 367/140 |
| 4,658,828 | 4/1987 | Dory | 128/660 |

FOREIGN PATENT DOCUMENTS 2140693A 12/1984 United Kingdom.
2187840 9/1987 United Kingdom.

Primary Examiner—Brian Steinberger
Attorney, Agent, or Firm—William A. Drucker

[57] ABSTRACT

An elastic pulse generator including a piezo-electric or magnetrostrictive transducer which is focussing or associated with a focussing device, having a plurality of elementary emitting surfaces generating elastic signals. These signals are superimposed, after propagation over a certain distance, in a focal region. Several groups of elementary emitting surfaces are periodically exciting at a predetermined rate with respective separate electric signals. The emitting surfaces belong to transducer elements electrically isolated from each other and having different transfer functions. Delay lines are provided for phase shifting the elastic signals emitted by the transducer elements.

10 Claims, 2 Drawing Sheets

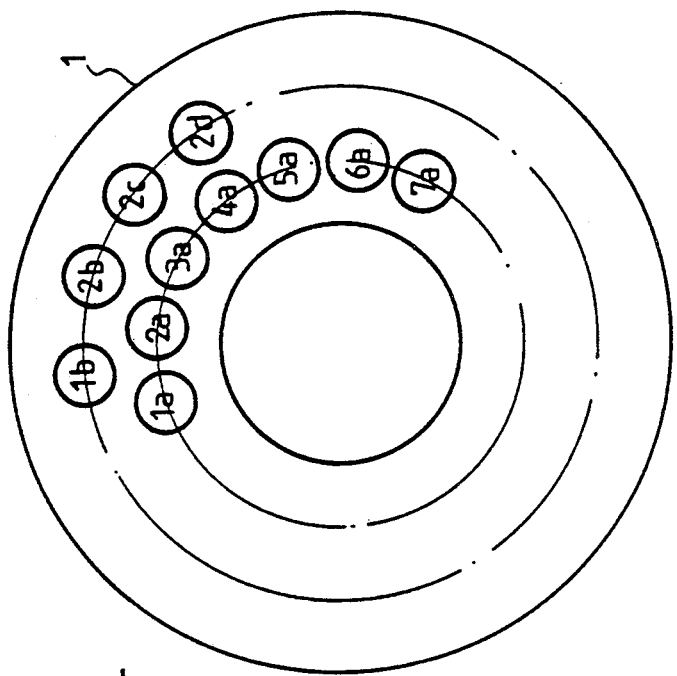
FIG.2
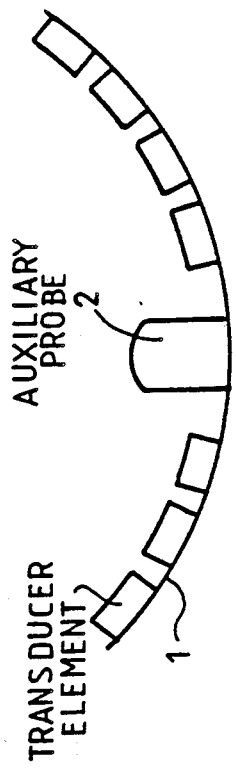
FIG.3
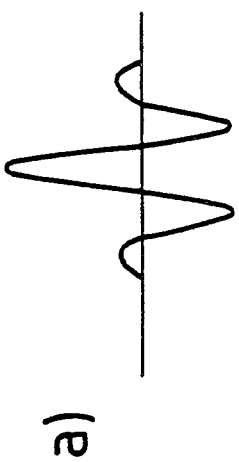
FIG.1
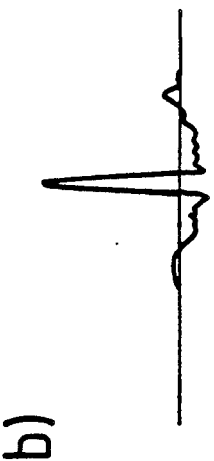
a)
b)

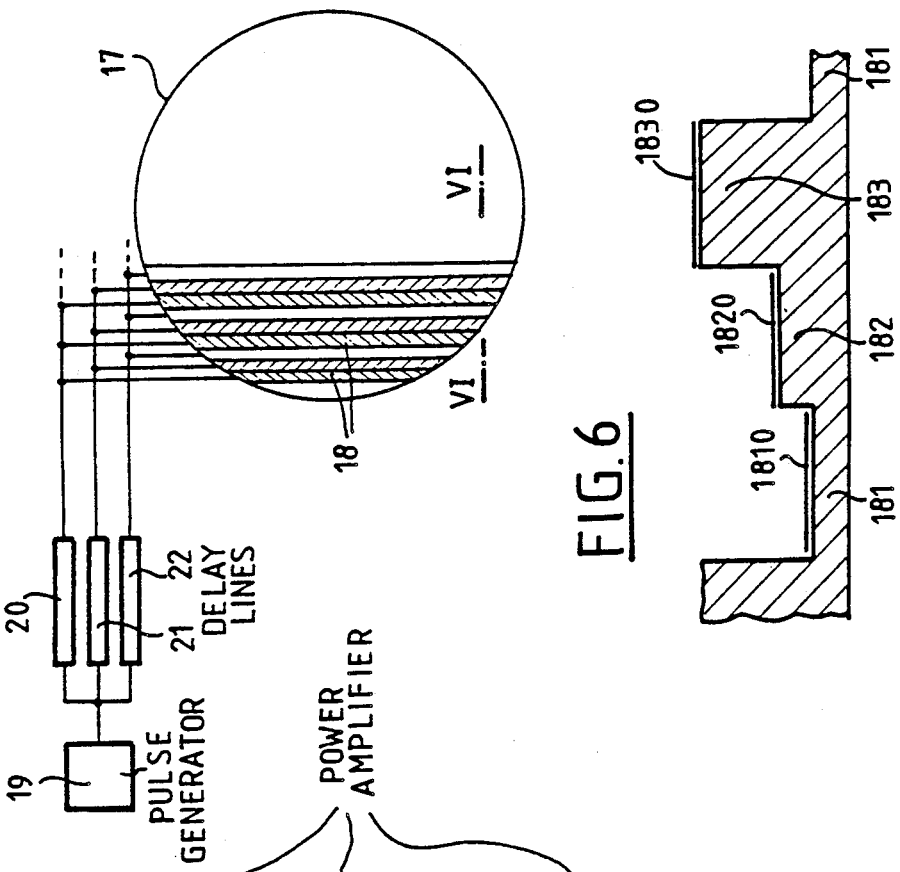
FIG.5
FIG.4
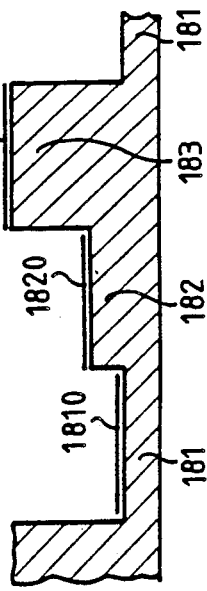
FIG.6

ELASTIC PULSE GENERATOR HAVING A DESIRED PREDETERMINED WAVE FORM

This application is a continuation-in-part of Ser No. 037,369, filed Apr. 13, 1987 now abandoned which is a division of Ser. No. 728,905 filed 4/30/85 now U.S. Pat. No. 4,658,828 which is a continuation-in-part of Ser. No. 674,889 filed 11/26/84, now U.S. Pat. No. 4,617,931.

BACKGROUND OF THE INVENTION

When elastic pulses, in particular high power elastic pulses, such as those used in extra corporeal lithotripsy, propagate in a coupling liquid, the negative peaks which their wave form inevitably comprises generate pressure variations within the liquid and, when the local pressure drops below the saturating vapor pressure, vapor filled cavities may be formed within the liquid. As soon as these vapor bubbles reach higher pressure regions, they are suddenly condensed.

The applicant has discovered that this cavitation phenomenon tends to slow down the propagation of any positive peak preceded by a negative peak and, consequently, to considerably reduce the power transmitted to the cells to be treated or to be examined by means of an elastic pulse generator and to cause different disturbances of the desired effects in the application of the elastic pulses to echography examination or to treatment by ultra-acoustic power concentration at a focal point. In extra-corporeal lithotripsy, the cavitation has the particularly important disadvantage of cause a prickly sensation which may reach the pain threshold.

SUMMARY OF THE INVENTION

The present invention provides an elastic pulse generator having a desired predetermined wave form, obtained by superimposing in a focal region of a piezo-electric or magnetostrictive transducer elementary, elastic waves having different frequency and phase characteristics generated separately by respective elementary emitting surfaces of the transducer themselves with surfaces have different transfer functions.

The elastic pulse generator of the invention includes a piezo-electric or magnetostrictive transducer, which is focussing or is associated with focussing means, having a plurality of elementary emitting surfaces generating elastic signals which are superimposed after propagation over a certain distance in a focal region and means for periodically exciting, at a given rate, several groups of elementary surfaces with respect separate brief electric signals and is characterized in that said emitting surfaces belong to transducer elements electrically isolated from each other and having different transfer functions and means for phase shifting the elastic signals emitted by the transducer elements.

Preferably, the excitation means are adapted so that said brief electric signals have different frequency spectra.

In a preferred embodiment, the resonance frequencies of the transducer elements are whole multiples of one of them (F), advantageously F, 2F, 3F and 4F or F, 2F and 4F and the phase shifts of each of them (Fn) with respect to a common arbitrary phase reference are equal to $-5/(4Fn)$.

In a first embodiment, the transducer is formed by a support in the shape of a spherical cap on the surface of which elementary ceramic piezo-electric transducers are distributed whose thicknesses are inversely proportional to the excitation frequencies.

Preferably, the excitation means includes generators of different frequencies, synchronized by the same synchronization signal which determines said emission rate and adjustably delay lines which form said phase shift means. In a second embodiment, the transducer is formed by a one piece ceramic machined to form elementary emissive surfaces of different thicknesses electrically isolated from each other.

The invention also provides a treatment method and, in particular, a method of extra-corporeal lithotripsy by means of elastic pulses, characterized by the reduction of the harmful, and in, particular, painful effects due to cavitation by substantial reduction of the amplitude of the negative peaks of said pulses with respect to those of the positive peaks.

BRIEF DESCRIPTION OF THE DRAWINGS

Other features as well as the advantages of the invention will clearly appear from the following description.

In the accompanying drawings:

FIG. 1 shows wave forms for explaining the method of the invention;

FIG. 2 is a schematical plan view of the emission phase of a transducer in the form of a spherical cup, of which FIG. 3 is a schematical sectional view through a plan of symmetry;

FIG. 4 is an excitation circuit diagram;

FIG. 5 shows a flat transducer assembly machined with the excitation circuit; and FIG. 6 is a partial sectional view through VI—VI of FIG. 5.

DESCRIPTION OF THE PREFERRED EMBODIMENT

In FIG. 1, a short duration elastic pulse is shown at (a) which is produced by means of a piezo-electric transducer such as presently constructed, when it is desired to generate a pulse accompanied by a minimum number of damped oscillations, whose rear face has been suitably damped, whereas blades for matching the acoustic impedances have been mounted on its front face. Such a pulse comprises half waves of opposite signs of the high excitation frequency of the transducer, and the presence of the negative half waves result in a significant loss of efficiency, due to cavitation, as soon as the emitted power is relatively high (which is the case for probes used in therapy).

It will be noted that it is indispensable for the polarity of the transducer to be chosen so that the first peak of significant amplitude is positive, for in the opposite case the cavitation caused by a first negative peak would prevent the propagation of the rest of the signal.

It can be seen in FIG. 1(a) that this first peak has an amplitude substantially lower than that of the second: the result is finally that all the power of the signal is not used and that cavitation may cause harmful effects.

It should be emphasized that even a theroretically perfect transducer, whatever the form of its excitation signal, will generate at least two half waves of opposite signs, because it necessarily comprises two emitting surfaces separated by a half wave length and emitting in phase opposition.

At (b) there is shown an elastic pulse produced by means of a piezo-electric transducer formed of a plurality of elements excited independently whose respective resonance frequencies are $F_1, F_2 \ldots F_n$, these elements being excited by electric pulses with respective carrier frequencies $F_1, F_2 \ldots F_n$ phase shifted with respect to an origin of the arbitrary phases by $-5/(4F_1)$, $-5/(4F_2)$, $-5/(4F_n)$. Experience shows that, if these electric signals have the same amplitude or closely related amplitudes and if the elements of the transducer are constructed to generate the acoustic wave form shown at (a) the superimposition of the acoustic signals thus generated gives the waveform shown at (b).

In this waveform, the negative half waves have a very reduced relative amplitude. Experience shows that it is sufficient to take, for example, four elements having frequencies F, 2F, 3F and 4. For even three elements having frequencies F, 2F, and 4F to obtain a sufficient predominance of the single positive half-wave.

When such elements are, for example, placed on a spherical cap, their paths as far as the center of the sphere which forms the focal center is identical and the acoustic signals therefore arrive at the focal center with the same relative phases as at the time of emission. They could be placed on a different surface, for example flat, and it would then be necessary to modify the phase shifts of the excitation signals to obtain focussing taking into account the differences of paths between the different elements.

The elements, which are excited by different frequencies, are phase shifted with respect to each other and can be greater in number than four (or divided into more than 4 groups each formed of elements excited by the same signal) and the frequencies and the phase shifts could be different from those which have been mentioned above by way of preferred example.

one of the objects of the invention is the generation of a predetermined brief acoustic wave shape (in practice, advantageously having the predominance of a single positive peak) by superimposing several elementary elastic waveforms. Such generation is obtained by superimposing, in the same region of space, individual elastic waves having at least different phase and frequency characteristics which are combined together to give the desired resulting waveform. In practice, by means of a computer assisted control for adjusting the frequency, phase and even amplitude parameters of the individual waveforms, the resultant simulated waveform is optimized by varying said parameters.

It should be emphasized that it would not be sufficient to vary the parameters of the electric signal for exciting a traditional transducer having a homogeneous emission surface because obtaining the desired result, for the pulse response of such a transducer would, at best, be of the type shown in FIG. 1(a).

On the other hand, with the heterogeneous transducer of the described type, in order to magnify a predominant peak, the different elements thereof can be excited with a single electric signal covering a large frequency spectrum and the appropriate phase shifts between the different individual elastic waveforms thus generated can further be obtained acoustically, i.e. by interposing in the path of each beam of elastic waves generated by the transducer blocks of a suitable shape of a material transparent to said waves, but in which they would propagate at a speed different from that of the transmission medium by means of which the transducer is normally coupled to the treated medium.

The solution described is however more convenient to carry out and allows easy adjustments.

In FIGS. 2 and 3, a spherical cap 1 has been shown made from aluminium alloy, the radius of the sphere being for example 40 cm and the height of the cap being 3.8 cm. On the internal surface of this cap are mounted, for example, 300 ceramic piezo-electric elements of cylindrical shape, each having, for example, a diameter of 20 mm. These elements are divided over three concentric circles, only two of which have been shown, in an annular zone which surrounds a central auxiliary transducer 2 whose function was described in U.S. Pat. No. 4,617,931.

Only the features which distinguish the lithotripsy emitter of the present invention from that of said patent will be described.

The elements of each of the sets $1a$–$2a$ …, $1b$–$2b$ … of the annular zone are divided into three groups: for example, the elements $1a$–$4a$ … $(3n+1)$ a form a first group having a resonance frequency of 300 kHz, the elements $2a$–$5a$ … $(3n+2)$ a form a second group having a resonance frequency of 600 kHz, the elements $3a$–$6a$ … $(3n+3)$a form a third group having a resonance frequency of 1200 kHz. The distribution of the frequencies for the elements corresponding rank for the other two annular sets is the same. The different frequencies correspond to cylindrical elements of different heights having respective resonance frequencies F, 2F and 4F, for example 10 mm for 300 kHz, 5 mm for 600 kHZ and 2.5 mm for 1200 kHz.

In FIG. 4, a synchronization generator 3 is shown which emits pulses whose duration is of the order of a microsecond and whose frequency is adjustable between 1/100 and 1 Hz for example.

These pulses are applied, through three adjustable phase shift circuits, 4, 5, 6, to three high frequency pulse generators, 7, 8, 9 corresponding respectively to the resonance frequencies of the three groups of elements, by way of example 300 kHz, 600 kHz and 1200 kHz respectively.

Generators 7, 8, 9 drive respectively power amplifiers 13, 14, 15 through respective separator stages 10, 11, 12.

Each power amplifier has as many separate stages in parallel as there are elements in each group for exciting the different elements of the same group separately and in parallel.

The phase shift circuits, 4, 5, 6, for example, formed from delay lines, are adjusted to obtain a waveform as close as possible to the one which is desired in accordance with the above indications. A computer 16 is shown symbolically which calculates and controls the adjustments, the waveforms of three synchronization signals and the signal resulting from the superimposition. This computer will act not only on the adjustment of the phase shift circuits but also on those of generators 7, 8, 9 for determining the three waveforms and their respective phase shifts.

Such a device would obviously make it possible to obtain a great variety of waveforms of the acoustic signal generated by the transducer assembly, including for magnifying for example the negative peaks in order to increase the cavitation phenomenon in non medical applications.

In the application to lithotripsy, the method, through the considerable reduction of cavitation, makes it possible to carry out firing at rates which could reach 150 Hz to reduce the present treatment time by a factor about 10.

By way of variation of the device which has just been described, the phase shifts, obtained electronically between the three synchronization signals, could be replaced by phase shifts obtained by introducing different path lengths of the acoustic signals generated by the three respective groups of transducers.

By way of example, such differences may be obtained by introducing suitable respective shims, made from a material capable of transmitting ultrasounds, between the surface of the cap 1 and the rear excitation surface of the cylindrical piezo-electric elements of the three groups.

In FIG. 5, a probe is shown which is used for echography and consequently has to generate acoustic pulses whose frequency spectrum is centered at 5 MHz.

This probe is formed by a piezo-ceramic disk 17, having for example, a diameter of 20 mm and a flat radiating or "front" face. On the other hand, its rear excitation face is machined to form a series of very fine parallel strips 18, of a width for example having 1 mm and of different thicknesses.

In FIG, 6, an enlarged and fragmentary view has been shown of a thickness of the disk representing a succession of groups of three strips such as 181, 182, 183 having respectively thicknesses of ¼ mm, ½ mm, and 1 mm.

Each of these strips is provided with an excitation electrode 1810, 1820, 1830 isolated from that of the adjacent strips.

In FIG. 6, a single electric pulse generator 19 has been shown connected to the respective electrodes 1810, 1820, 1830 of FIG. 6 through three adjustable delay lines 20, 21, 22. More precisely, the output of each delay line 20 is connected to all the electrodes of the strips of the same thickness of the successive groups. Of course, the ground wires, not shown, are connected to a single electrode, not shown, fixed to the front face.

Thus, three assemblies of piezo-electric transducers are formed having respective resonance frequencies of 10 MHz, 5 Mhz, and 2.5 Mhz.

In a way known per se, the rear face of the disk will be further advantageously provided with a block for damping parasitic oscillations, whereas the front face will be machined for positioning impedance matching blades.

The delays are adjusted to correspond to the desired phase shifts of the three acoustic signals of different frequencies generated by the three respective assemblies, as already explained. The excitation signal supplied by generator 19 must have a frequency spectrum covering the values 10 MHz, 5 MHz and 2.5 MHz.

This embodiment is appropriate to the construction of probes working at high frequencies (several megahertz): it avoids the delicate manufacture of independent individual piezo-electric elements of very small size.

Such a transducer is not focussing and will therefore be associated, in order to superimpose the individual elastic waves, with a focussing means, for example an acoustic lens.

What is claimed is:

1. An elastic pulse generator comprising:
   (a) at least two transducer elements electrically isolated from each other and having different transfer functions,
   (b) electric signal generator means driving said transducer elements for generating from each said transducer element an elastic signal beam, each said elastic signal beam having a different frequency spectrum,
   (c) phase shifting means for mutually phase shifting each said elastic signal, and
   (d) focusing means for focusing each said elastic signal beam at a common focal region.

2. The generator as claimed in claim 1, wherein the resonance frequencies Fn of different ones of said transducer elements are whole multiple n of the resonance frequency F of one of said transducer elements and the phase shifts between different ones of said transducer elements with respect to a common arbitrary phase reference is $-5/(4Fn)$.

3. The elastic pulse generator as claimed in claim 2, wherein said transducer elements include a first transducer element having a resonance frequency F, a second transducer element having a resonance frequency 2F and a third transducer element having a resonance frequency 4F, and said phase shifting means respectively shift the respective elastic signals by $-5/(4F)$, $-5/(8F)$ and $-5/(16F)$ with respect to a common arbitrary phase reference.

4. The elastic pulse generator as claimed in claim 2, wherein said transducer elements include a first transducer element having a resonance frequency F, a second transducer element having a resonance frequency 2F, a third transducer element having a resonance frequency 3F and a fourth transducer element having a resonance frequency 4F and said phase shifting means respectively shift the respective elastic signals by $-5/(4F)$, $-5/(8F)$, $5/(12F)$, $-5/(16F)$.

5. An elastic pulse generator as claimed in claim 1, wherein each said transducer element has a different resonance frequency and said electric signal generator means includes two pulse generators generating pulses having a fundamental frequency equal to one of said resonance frequencies.

6. An elastic pulse generator as claimed in claim 1, wherein said transducer elements have respectively different resonance frequencies and said electric signal generator means generate electric signals having a frequency spectrum comprising said resonance frequencies.

7. An elastic pulse generator as claimed in claim 6, wherein said phase shifting means comprise electric delay means connecting said electric signal generator means to said transducer elements.

8. An elastic pulse generator as claimed in claim 1, wherein said phase shifting means are acoustic means intercepting the respective elastic signal beams for modifying the propogation time thereof between said focusing means and said focal region.

9. An elastic pulse generator as claimed in claim 1, wherein said transducer elements have respective transmissive surfaces located at different distances from said focal region.

10. An elastic pulse generator as claimed in claim 1, wherein said transducer elements are piezoelectric ceramic discs having different thicknesses and supported on a common spherical cap.

* * * * *